United States Patent
Tortorella et al.

(10) Patent No.: US 9,810,609 B2
(45) Date of Patent: Nov. 7, 2017

(54) TRANSFER AND STORAGE OF BIOLOGICAL MATERIAL

(71) Applicant: GE HEALTHCARE UK LIMITED, Little Chalfont (GB)

(72) Inventors: Stevan Paul Tortorella, Wells, ME (US); William A. Garwood, Saint Paul, MN (US)

(73) Assignee: GE Healthcare UK Limited, Little Chalfont (GB)

(*) Notice: Subject to any disclaimer, the term of this patent is extended or adjusted under 35 U.S.C. 154(b) by 90 days.

(21) Appl. No.: 14/765,009

(22) PCT Filed: Jan. 28, 2014

(86) PCT No.: PCT/EP2014/051612
§ 371 (c)(1),
(2) Date: Jul. 31, 2015

(87) PCT Pub. No.: WO2014/118166
PCT Pub. Date: Aug. 7, 2014

(65) Prior Publication Data
US 2015/0369707 A1    Dec. 24, 2015

Related U.S. Application Data

(60) Provisional application No. 61/758,958, filed on Jan. 31, 2013.

(51) Int. Cl.
| | | |
|---|---|---|
| *G01N 1/28* | (2006.01) | |
| *C12M 1/00* | (2006.01) | |
| *C12Q 1/68* | (2006.01) | |
| *C12N 15/10* | (2006.01) | |

(52) U.S. Cl.
CPC ............ *G01N 1/286* (2013.01); *C12M 45/22* (2013.01); *C12Q 1/6806* (2013.01); *C12N 15/1003* (2013.01)

(58) Field of Classification Search
CPC ..... G01N 1/286; C12Q 1/6806; C12M 45/22; C12N 15/1003
See application file for complete search history.

(56) References Cited

U.S. PATENT DOCUMENTS

| | | | | |
|---|---|---|---|---|
| 5,898,071 A | * | 4/1999 | Hawkins ............ | C12N 15/1013 435/91.1 |
| 2012/0237925 A1 | * | 9/2012 | Isely .................. | C12N 1/066 435/6.1 |

FOREIGN PATENT DOCUMENTS

| | | |
|---|---|---|
| DE | 10260324 A1 | 9/2003 |
| WO | 9509701 A1 | 4/1995 |
| WO | 03055976 A2 | 7/2003 |

OTHER PUBLICATIONS

Adugna et al. (Journal of Agricultural Science and Technology, Feb. 2011, vol. 5, No. 2.*

(Continued)

*Primary Examiner* — Sally Merkling

(57) ABSTRACT

Apparatus for transferring biological material onto storage media, said apparatus comprising a powered hand held device including a powered hammer arrangement, the apparatus further comprising an anvil arrangement and a storage media accepting area between the hammer and the anvil, the apparatus being operable such that in use the storage media is repeatedly compressed between the hammer and the anvil by blows from the hammer.

13 Claims, 1 Drawing Sheet

(56) References Cited

OTHER PUBLICATIONS

International Search Report and Written Opinion dated Jun. 30, 2014 which was issued in connection with PCT Patent Application No. EP2014/051612 which was filed on Jan. 28, 2014.
GE Healthcare Life Sciences: "Your forensic samples, our experience", Sep. 1, 2011.
Whatman: "EasiCollect tm", Oct. 1, 2007, pp. 1-1
Nzungize et. al.: "Introgression of Pythium root rot resistance gene into Rwandan susceptible common bean cultivators", African Journal of Plant Science, Jan. 1, 2011, pp. 193-200.
Roy et. al. : "Detection of Plant Genes, Gene Expression and Viral RNA from Tissue Prints on FTA Cards", Plant Molecular Biology Reporter, vol. 23, Dec. 2005.
Adugna et. al.: "Optimization of a High Throughput, Cost Effective, and All-stage DNA Extraction Protocol for Sorghum (Sorghum bicolor)", Feb. 1, 2011, pp. 1939-1250.

\* cited by examiner section on II-II

TRANSFER AND STORAGE OF BIOLOGICAL MATERIAL

BACKGROUND OF THE INVENTION

Embodiments of the present invention relate to apparatus for the transfer of biological material onto biological storage media, such as treated card or paper. Embodiments of the present invention relate relates also to methods for transferring such materials onto the media.

It is known to transfer plant and like biological material onto treated storage card or paper for capturing biological information, for example when examining rare species in remote locations. Commercially available biological storage media is sold as a sample storage card and is supplied by GE Healthcare under the brand name FTA. This card is chemically treated to preserve DNA material. A known technique for transferring biological material onto the card involves vigorously rubbing the plant material onto the treated card in order to transfer cells from the plant onto the paper. The cells are generally lysed by the chemical treatment on the card and DNA material within the lysed cells becomes bound to the card. The DNA material can be sequenced later at a laboratory, without the need to further preserve the plant material, and without the need to store the card at low temperatures.

However, this technique is time consuming and laborious. Also, the risk of contaminating the collected DNA is high because manual steps are involved. Further, consistent transfer of material is very difficult because the manual steps are not always performed with the same degree of rubbing force or for the same length of time, which in turn leads to inconsistencies in the quantity and quality of plant material transferred. Embodiments of the present invention address the above problems.

SUMMARY OF INVENTION

According to one aspect, the invention provides, apparatus for transferring biological material onto biological storage media, said apparatus comprising a powered hand held device including a powered hammer element, said apparatus further comprising an anvil portion and a storage media accepting area between the hammer and said anvil, the apparatus being operable such that in use the storage media is repeatedly compressed between the hammer and the anvil by the hammer.

In an embodiment, the anvil is adjustable in position relative the hammer.

Conveniently, said adjustable relative position affords frictional holding of the storage media between the anvil and the hammer or a portion of the apparatus adjacent the hammer.

In an embodiment, the hammer includes a moving portion, having a repeatable path of powered motion, and a head portion generally in engagement with the storage media, and said compression is achieved by the striking of the head portion by the moving portion.

In an embodiment, the repeatable path of motion is reciprocating motion.

In an embodiment, the moving portion is powered to move at between 1 and 100 reciprocations per second, more particularly, about 60 reciprocations per second.

According to an embodiment of the present invention, the velocity of the moving portion is adjustable to vary the media compression force.

In an embodiment of the present invention, the anvil is detachable from the device, and more particularly, the device is a battery powered percussive tool including the hammer.

In an embodiment, the tool includes a handle and an operating switch, and a head portion including the hammer, to which is fitted the anvil.

BRIEF DESCRIPTION OF THE DRAWINGS

Embodiments of the present invention can be put into effect in numerous ways. By way of example, embodiments are described below, with one example being illustrated in the drawings, wherein.

DETAILED DESCRIPTION OF THE DRAWINGS

Figure 1:
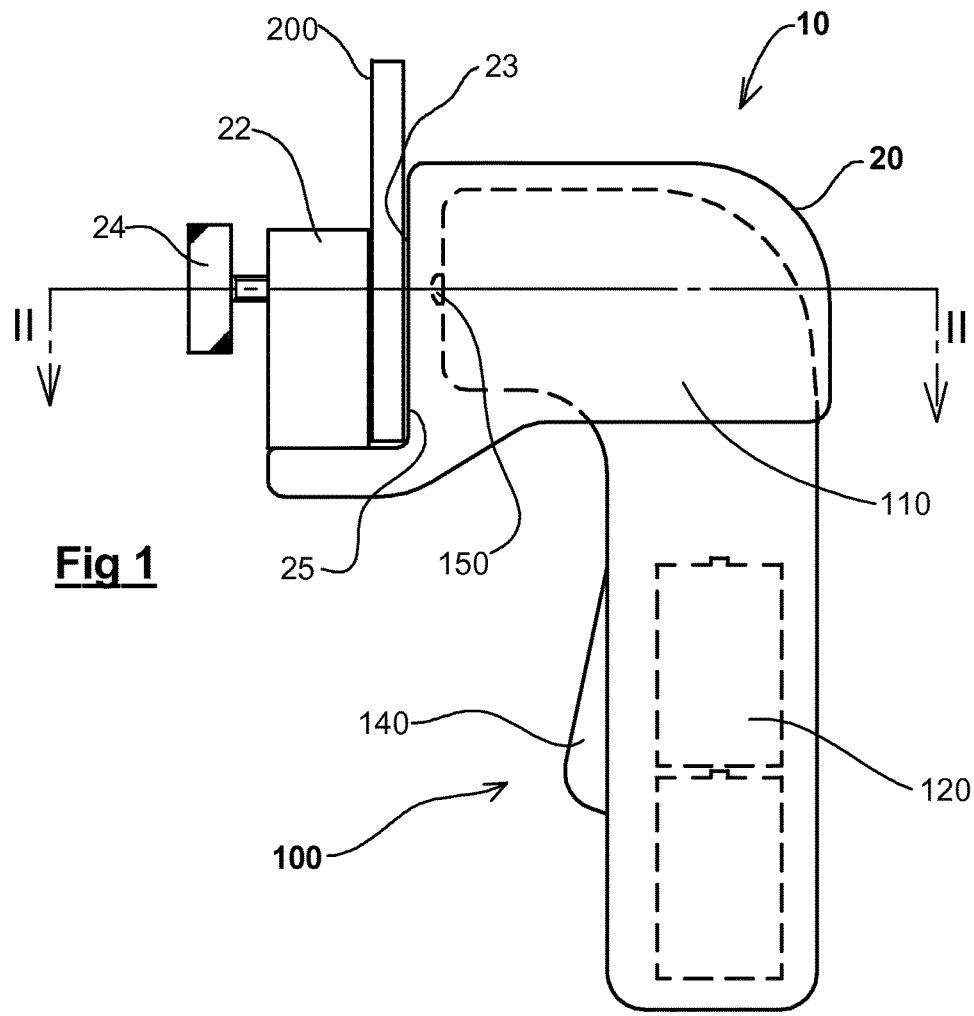
FIG. 1 shows a side view of an embodiment.

Referring to FIG. 1 there is shown apparatus 10 which includes a commercially available device 100 known as an 'auto hammer' used conventionally for driving nails or pins. This device includes a head 110 and a handle 120 which houses batteries 130. An on-off switch 140 is used to operate the device 100. In operation, the device has a hammer arrangement 150 which will reciprocate at around 60 impacts per second.

An additional, an anvil construction 20 has been added to the head 110 of the device 100. The anvil 20 sits snuggly on the head 110 and accepts biological samples storage media, in this case in the form of an FTA brand sample collecting card 200 in a slot 23. The anvil further includes an adjustable anvil face 22, moveable by means of a thumb screw 24, to gently hold the card 200 in place between the anvil face 22 and its opposing face 25.

Figure 2:
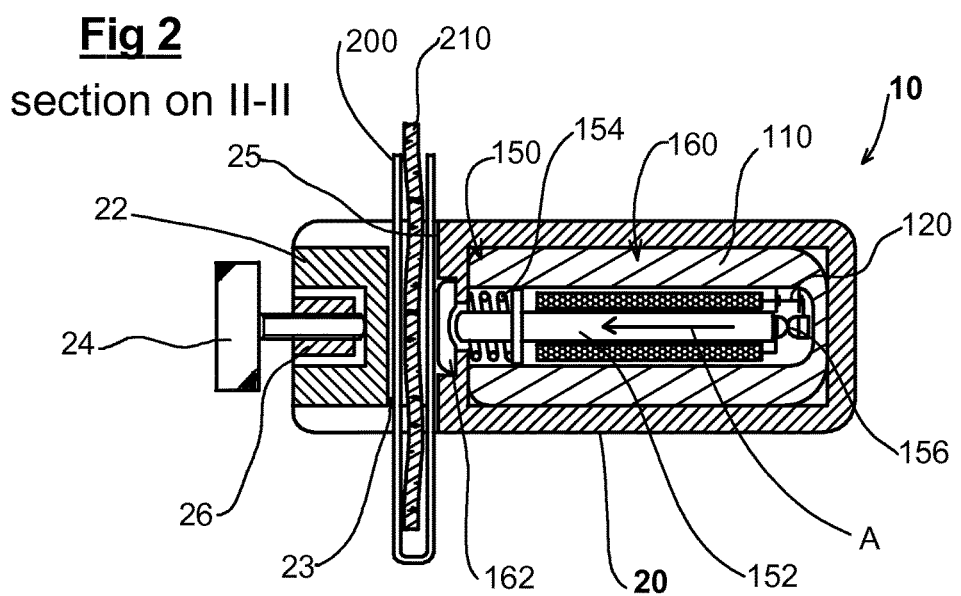
FIG. 2 shows a cross sectional plan view of the embodiment.

Referring additionally to FIG. 2, there is shown a section through the apparatus 10 at line II-II in FIG. 1. The anvil 20 is shown in more detail having a post 26 which supports the thumbscrew 24, in turn supporting the anvil face 22. The card 200 is shown folded around a plant specimen 210 ready to be compressed. A possible mechanism for the auto hammer 100 is shown schematically. The mechanism includes a solenoid 160 for electrically driving a moving portion 152 in the direction of arrow A. This moving portion 152 is connected to an electrical switch 156 which disconnects as it moves forwards, so it is then forced in the opposite direction by a return spring 154. The solenoid reciprocates in the manner of an electric bell mechanism to repeatedly hit a hammer head 162, which in turn transmits a repeated compression force into the card 200 and plant sample 210, thereby crushing the plant material and causing plant cell material to transfer to the sample card 200.

In practise, the mechanism works well by compressing the card and plant material at around 60 blows per second, although it is envisaged that slower reciprocations, for example 1 blow per second will yield good results, particularly for succulent plants, and faster repetitions, for example 100 blows per second could be employed, particularly for dry plant material such as waxy leaves or dead plant material. In this case the reciprocating speed can be adjusted by altering the voltage applied to the solenoid, and/or by moving the contacts of the switch 156, and/or by adjusting the position of the return spring 154.

It is envisaged that the slot 23 illustrated is of sufficient dimensions to allow the card 200 to be moved relative to the hammer head 162, so that multiple sample attempts can be performed on one card. For example, the card could be moved so that one of 4 discrete locations on the card is compressed to provide four areas on the card where biological material is stored. Additionally, it can be seen that the card 200 is folded around the plant 210, which offers less chance of contaminating the plant material during the compression steps.

Experiments have shown a quicker transfer of plant material onto FTA cards compared with conventional manual transfer. A period of 1 to 10 seconds is enough to transfer sufficient material onto the card, with about 5 seconds being about right for most plant materials. Also the consistency of transfer is visually better than prior manual techniques.

Although one embodiment only has been illustrated, it will be apparent to the skilled addressee that modifications, variants, additions and omissions are possible within the scope and spirit of the invention defined herein.

For example, in the embodiment shown, an electrically powered solenoid type mechanism is shown, but other electrically powered means to produce a hammer impact are possible. For example, a rotary or rocking mechanism could be employed, providing a blow during rotation or pivoting. The rotary mechanism could be a cam driven by an electric motor and providing energy to drive the hammer. It is envisaged that the auto hammer or an alternative mechanism, are driven by electricity, more particularly stored electricity from batteries, and more particularly rechargeable batteries.

Alternatively, other sources of power could be used, for example, pneumatic or hydraulic power could be employed. In the case of a pneumatic powered device, a compressed gas cylinder could be used to power a known pneumatic reciprocating mechanism, to provide the hammer blows needed to transfer the plant material to the cards. Such known pneumatic reciprocating mechanism are conventionally employed descaling tools and rivet guns.

In the embodiment shown, a separate auto hammer device and anvil arrangement are shown. However, where economic factors allow, a customised device could be produced incorporating the auto hammer device and the anvil as one moulding or one unit.

Whilst embodiments of the present invention can be applied for collecting plant samples, it will be apparent that other biological samples could be collected too, for example biological material from insects or other animal specimens could be collected.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus for transferring a biological material onto a storage media, said apparatus comprising a powered hand held device including a powered hammer arrangement, said apparatus further comprising an anvil arrangement and a storage media accepting area in the form of a slot between said hammer arrangement and said anvil arrangement, the apparatus being operable such that in use the storage media in a form of a sample collection card is repeatedly compressed between the hammer and the anvil by blows from the hammer.

2. The apparatus according to claim 1, wherein the anvil is adjustable in position relative the hammer.

3. The apparatus according to claim 2, wherein the storage media is held between the anvil and the hammer or a portion of the apparatus adjacent the hammer.

4. The apparatus according to claim 1, wherein the hammer includes a moving portion, having a repeatable path of powered motion, and a head portion generally in engagement with the storage media, and said compression is achieved by striking of the head portion by the moving portion.

5. The apparatus according to claim 4, wherein the repeatable path of powered motion is a reciprocating motion.

6. The apparatus according to claim 4, wherein the moving portion is powered to move at between 1 and 100 reciprocations per second, more preferably, about 60 reciprocations per second.

7. The apparatus according to claim 1, wherein the velocity of the moving portion is adjustable to vary a media compression force.

8. The apparatus according to claim 1, wherein the anvil is detachable from the device.

9. The apparatus according to claim 1, wherein the device is a battery powered percussive tool including the hammer.

10. The apparatus according to claim 9, wherein the tool includes a handle and an operating switch, and a head portion including the hammer, to which is fitted the anvil.

11. A method for transferring a biological material onto a storage media in a form of a sample collection card, the method comprising:
    a) providing a powered hammer and an anvil;
    b) placing the storage media on each side of a biological sample;
    c) placing the storage media and the biological sample in a storage media accepting area in a form of a slot between the hammer and the anvil; and
    d) repeatedly impacting the hammer toward the anvil with sufficient blows and a sufficient number of times to transfer the biological material from the sample to the storage media.

12. The method according to claim 11 wherein, step d) includes at least one of the following:
    i) impacting at 1 to 100 blows per second; and
    ii) impacting for between 1 and 10 seconds.

13. A kit comprising: an apparatus for transferring a biological material onto a storage media in a form of a sample collection card, said apparatus comprising a powered hand held device including a powered hammer arrangement, the apparatus further comprising an anvil arrangement and a storage media accepting area in a form of a slot between said hammer arrangement and said anvil arrangement, the apparatus being operable such that in use the storage media is repeatedly compressed between the hammer and the anvil by blows from the hammer; and the storage media providing storage for the biological material transferred thereto by the apparatus.

* * * * *